(12) United States Patent
Jeon (10) Patent No.: US 9,179,878 B2
(45) Date of Patent: Nov. 10, 2015

(54) NON-ROTATIONAL COMPUTERIZED TOMOGRAPHY SYSTEM

(75) Inventor: In Su Jeon, Gwangju (KR)

(73) Assignee: Industry Foundation of Chonnam National University, Gwangji (KR)

( * ) Notice: Subject to any disclaimer, the term of this patent is extended or adjusted under 35 U.S.C. 154(b) by 220 days.

(21) Appl. No.: 14/000,259

(22) PCT Filed: Jan. 5, 2012

(86) PCT No.: PCT/KR2012/000123
§ 371 (c)(1),
(2), (4) Date: Aug. 19, 2013

(87) PCT Pub. No.: WO2013/085098
PCT Pub. Date: Jun. 13, 2013

(65) Prior Publication Data
US 2013/0329852 A1    Dec. 12, 2013

(30) Foreign Application Priority Data
Dec. 9, 2011   (KR) .................. 10-2011-0131452

(51) Int. Cl.
*A61B 6/03* (2006.01)
*A61B 6/00* (2006.01)

(52) U.S. Cl.
CPC ............... *A61B 6/035* (2013.01); *A61B 6/032* (2013.01); *A61B 6/4014* (2013.01)

(58) Field of Classification Search
CPC .......... A61B 6/03; A61B 6/032; A61B 6/035; A61B 6/08; A61B 6/587; A61B 6/588; A61B 6/4007; A61B 6/4014; G01N 2223/419; G01N 23/046; G01V 5/005
See application file for complete search history.

(56) References Cited

U.S. PATENT DOCUMENTS 5,166,966 A * 11/1992 Steinmeyer .................. 378/156
6,801,594 B1 * 10/2004 Ali et al. ............................ 378/4

(Continued)

FOREIGN PATENT DOCUMENTS

| DE | 9012435 U1 * | 1/1992 | .............. A61B 6/04 |
|---|---|---|---|
| JP | 2005-510278 A | 4/2005 | |
| JP | 2007-502652 A | 2/2007 | |
| JP | 2010-234003 A | 10/2010 | |

OTHER PUBLICATIONS

Hudson et al., Accelerated Image Reconstruction Using Ordered Subsets of Projection Data, Dec. 1994, IEEE Transactions on Medical Imaging, vol. 13, No. 4, p. 601.*

(Continued)

*Primary Examiner* — Irakli Kiknadze
*Assistant Examiner* — Julio M Duarte-Carvajalino
(74) *Attorney, Agent, or Firm* — Lucas & Mercanti, LLP (57) ABSTRACT

A non-rotational CT system according to the present invention comprises: a plurality of X-ray generation units which are radially arranged by being spaced at certain intervals around an inspected object, and in which position correcting sensors are equipped on one side thereof; a plurality of X-ray detection units which are arranged in separated spaces between the X-ray generation units, are provided alternately with the X-ray generation units, and in which position correcting sensors are equipped on one side thereof; a control unit which receives signals from the position correcting sensors equipped in the X-ray generation units and the X-ray detection units, and adjusts the positions of each of the X-ray generation units and the X-ray detection units which face each other to precisely correspond with each other; a data processing unit which stores two-dimensional X-ray images obtained from the X-ray detection units, and applies an image interpolation technique to calculate two-dimensional X-ray images between two directions; and an image processing unit which converts data of the data processing unit into CT image data.

11 Claims, 9 Drawing Sheets

(56) References Cited

U.S. PATENT DOCUMENTS

| | | |
|---|---|---|
| 2005/0175143 A1 | 8/2005 | Miyazaki et al. |
| 2005/0175151 A1* | 8/2005 | Dunham et al. ............. 378/122 |
| 2006/0023832 A1* | 2/2006 | Edic et al. ........................ 378/7 |
| 2007/0133749 A1* | 6/2007 | Mazin et al. .................. 378/147 |

OTHER PUBLICATIONS

EPO machine translation of DE9012435 U1.*
International Search Report of PCT/JP2012/000123 dated Dec. 28, 2012.

* cited by examiner

CT image using 120
real projection images

CT image using 60
real projection images

CT image using 30
real projection images

CT image using 15
real projection images

Figure 7

CT image obtained from
30 real projection images

CT image obtained from
30 real plus 30 interpolated

CT image obtained from
15 real projection images

CT image obtained from
15 real plus 45 interpolated

Figure 8

CT image using 120
real projection images

CT image using 3
real projection images

Figure 9

Pig leg

CT image using 120 real projection images

CT image using 5 real projection images

CT image using 3 real projection images

NON-ROTATIONAL COMPUTERIZED TOMOGRAPHY SYSTEM

CROSS-REFERENCE TO RELATED APPLICATIONS

This application is a 371 of PCT/KR 2012/000123 filed on Jan. 5, 2012, which claims the priority of KR application Ser. No. 10-2011-0131452 filed on Dec. 9, 2011, the contents of each of which are incorporated herein by reference.

TECHNICAL FIELD

The present invention relates, in general, to a Computerized Tomography (CT) system, which does not require the rotation of a target or equipment upon CT scanning and, more particularly, to a non-rotational CT system, which includes a plurality of X-ray generation units and a plurality of X-ray detection units.

BACKGROUND ART

A Computerized Tomography (hereinafter referred to as "CT") scanner is equipment for passing a predetermined dose of X-ray radiation through a region of a body to be imaged, allowing an X-ray detector to acquire a variation in the intensity of passed X-rays, obtain X-ray absorption factors at respective points on the body region to be imaged, and reconfiguring an image from the X-ray absorption factors.

A conventional X-ray CT scanner goes through a process for rotating an object using one or two sources and detectors or for rotating the sources and detectors around the object, acquiring two-dimensional (2D) X-ray images at various angles, and then converting the 2D images into CT images.

However, such a CT scanner is limited in that 2D images at various angles must be taken so as to acquire a cross-section image at one position, and in that, in this case, a lot of time is required for such imaging and it is possible to perform CT scanning only on an examination target which is in a static state.

In particular, it is impossible to perform real-time CT scanning on objects in motion and objects currently being deformed by an external load, that is, objects having rapid variations in a short period of time.

Further, in the case of a typical X-ray CT scanner, 2D X-ray images must be taken in a large number of directions, so that a problem arises in that, when such an X-ray CT scanner is used to examine patients in hospitals, X-ray radiation exposure to the patients increases, and the inconvenience of patients increases because a lot of time is required for X-ray imaging.

DISCLOSURE

Technical Problem

Accordingly, the present invention has been made keeping in mind the above problems, and an object of the present invention is to provide a non-rotational CT system, which can acquire X-ray images of various targets every moment based on an arbitrary time point and then construct CT images of the targets at respective time points using a minimum number of acquired 2D X-ray images and an image interpolation technique.

Technical Solution

In order to accomplish the above object, the present invention provides a non-rotational Computerized Tomography (CT) system, including a plurality of X-ray generation units spaced apart from an examination target by a regular distance and radially arranged around the examination target, the X-ray generation units having position correction sensors arranged in portions thereof; a plurality of X-ray detection units arranged in separated spaces between the X-ray generation units and installed to alternate with the X-ray generation units, the X-ray detection units having position correction sensors arranged in portions thereof; and a control unit configured to receive signals from the position correction sensors arranged on the X-ray generation units and the X-ray detection units, and adjust positions of corresponding X-ray generation units and X-ray detection units so that the corresponding X-ray generation units and X-ray detection units exactly face each other.

In this case, each of the X-ray generation units may include an X-ray guide provided on a first side thereof towards the examination target.

Preferably, each of the X-ray detection units may include an X-ray guide provided on a first side thereof towards the examination target, and may be configured to allow X-rays generated by an X-ray generation unit exactly facing the corresponding X-ray detection unit to pass through the examination target and to be then transferred only to a designated X-ray detection unit.

Preferably, the X-ray guides of the X-ray generation units and the X-ray detection units may be made of an X-ray absorbing material, each of the X-ray generation units may include a Kα X-ray filter disposed at an end of the X-ray guide of the X-ray generation unit and configured to function to prevent mutual interference between X-rays having Kα and Kβ characteristics, and each of the X-ray detection units may include an elastic scattering prevention filter arranged at an end of the X-ray guide of the X-ray detection unit.

Preferably, the control unit may receive signals from the position correction sensors, and adjust positions and directions of the X-ray generation units and the X-ray detection units so that X-rays generated by one X-ray generation unit pass through the examination target and can then be transferred only to an X-ray detection unit designated to face the corresponding X-ray generation unit.

In order to accomplish the above object, an embodiment of the present invention provides a non-rotational Computerized Tomography (CT) system, including a plurality of X-ray generation units spaced apart from an examination target by a regular distance and radially arranged around the examination target, the X-ray generation units having position correction sensors arranged in portions thereof; a plurality of X-ray detection units arranged in separated spaces between the X-ray generation units and installed to alternate with the X-ray generation units, the X-ray detection units having position correction sensors arranged in portions thereof; a control unit configured to receive signals from the position correction sensors arranged on the X-ray generation units and the X-ray detection units, and adjust positions of corresponding X-ray generation units and X-ray detection units so that the corresponding X-ray generation units and X-ray detection units exactly face each other; a data processing unit configured to store 2D X-ray images acquired by the X-ray detection units and calculate 2D X-ray images between two directions using an image interpolation technique; and an image processing unit configured to convert data of the data processing unit into CT image data.

In this case, each of the X-ray generation units may include an X-ray guide provided on a first side thereof towards the examination target.

Preferably, each of the X-ray detection units may include an X-ray guide provided on a first side thereof towards the examination target, and may be configured to allow X-rays generated by an X-ray generation unit exactly facing the corresponding X-ray detection unit to pass through the examination target and to be then transferred only to a designated X-ray detection unit.

Preferably, the X-ray guides of the X-ray generation units and the X-ray detection units may be made of an X-ray absorbing material, each of the X-ray generation units may include a Kα X-ray filter disposed at an end of the X-ray guide of the X-ray generation unit and configured to function to prevent mutual interference between X-rays having Kα and Kβ characteristics, and each of the X-ray detection units may include an elastic scattering prevention filter arranged at an end of the X-ray guide of the X-ray detection unit.

Preferably, the control unit may receive signals from the position correction sensors, and adjust positions and directions of the X-ray generation units and the X-ray detection units so that X-rays generated by one X-ray generation unit pass through the examination target and can then be transferred only to an X-ray detection unit designated to face the corresponding X-ray generation unit.

Further, the 2D X-ray data acquired using the image interpolation technique may be obtained by converting images into CT image data using an Ordered Subset Expectation Maximization (OSEM) technique.

Advantageous Effects

In accordance with the non-rotational CT system according to the present invention, the internal structure of a target in a continuously varying situation can be examined, so that there are advantages in that when an industrial material is set as a target, it is possible to analyze in real time the internal structure of a material currently being deformed and analyze the structure of the cross-section of a target in motion, and in that when a patient is set as a target for medical treatment, it is possible to remarkably reduce radiation exposure to the patient, and it is possible to analyze the real-time deformed state of the cross-section of a blood vessel, a variation in the internal structure or the like of the heart while the heart is beating, the shapes of joints having motions, etc., thus enabling more substantial image diagnostic data of a patient to be acquired.

BEST MODE

The above object, features, and other advantages of the present invention will be more clearly understood from the following detailed description taken in conjunction with the accompanying drawings. Hereinafter, a non-rotational CT system according to embodiments of the present invention will be descried in detail with reference to the attached drawings.

Figure 1A:
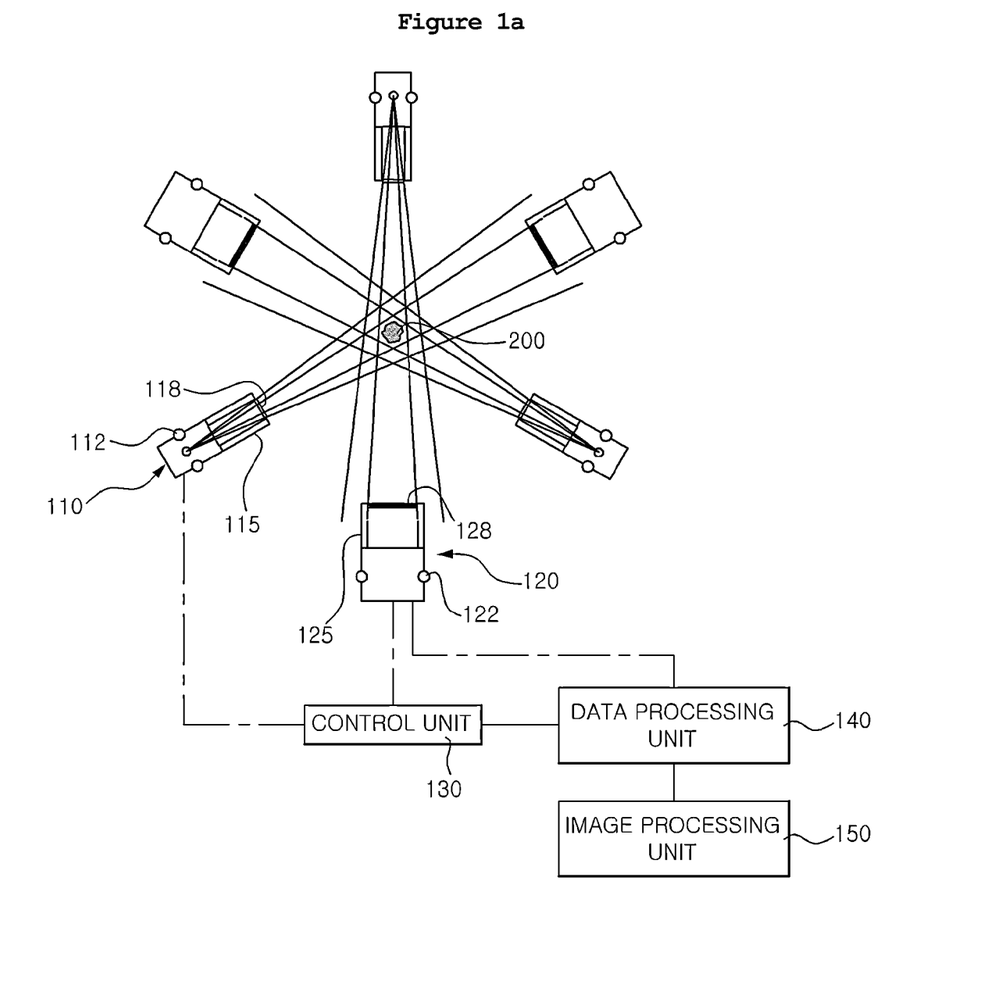
FIGS. 1a and 1b are configuration diagrams showing a non-rotational CT system according to an embodiment of the present invention.
Figure 1B:
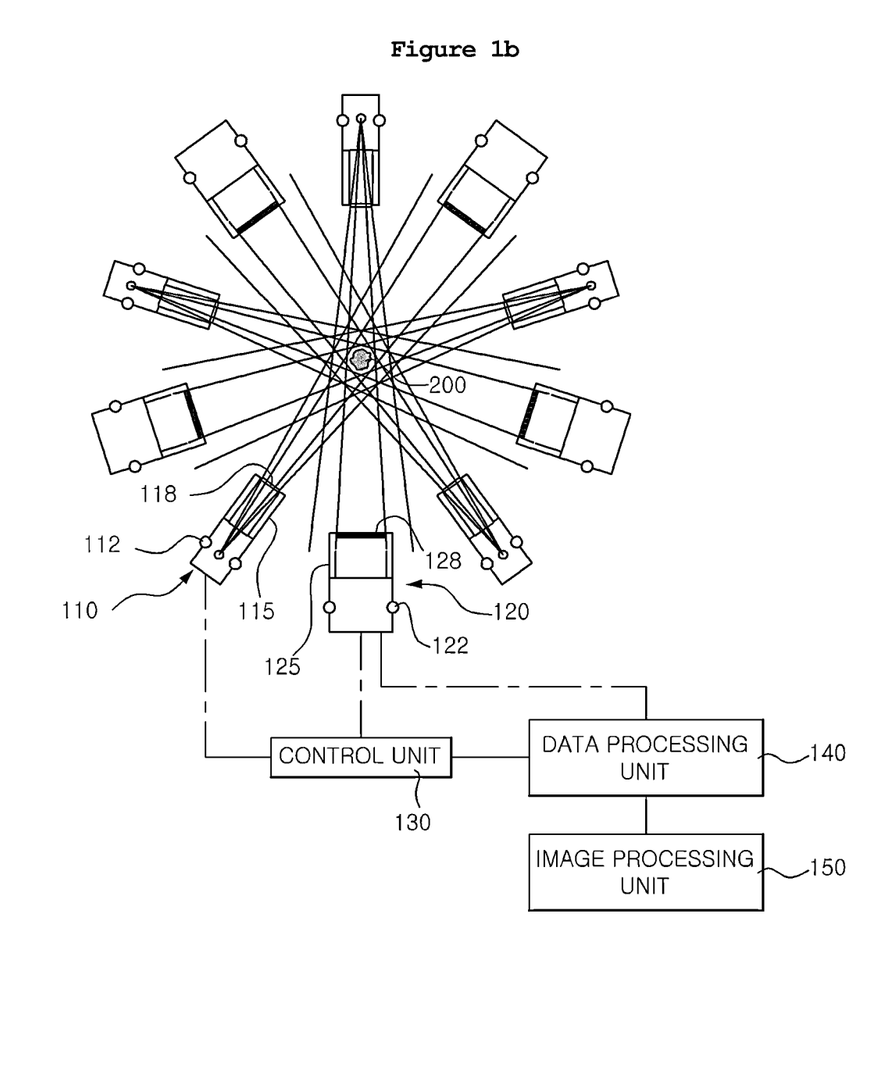
Figure 2:
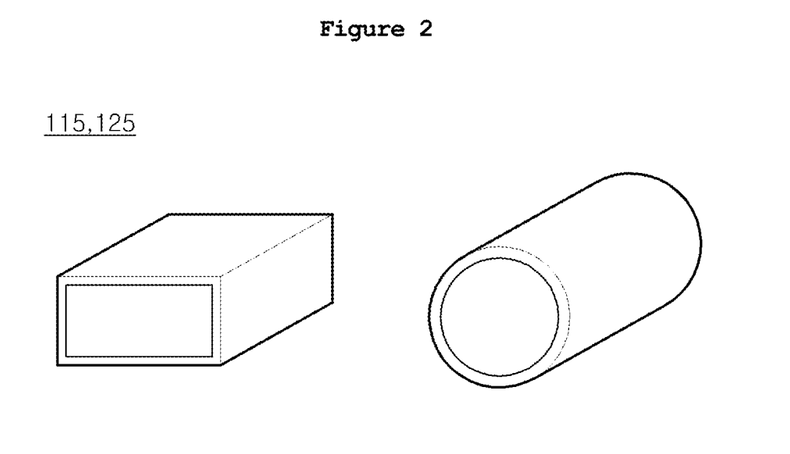
FIG. 2 is a conceptual diagram showing X-ray guides having various shapes applied to a non-rotational CT system according to an embodiment of the present invention.
Figure 3:
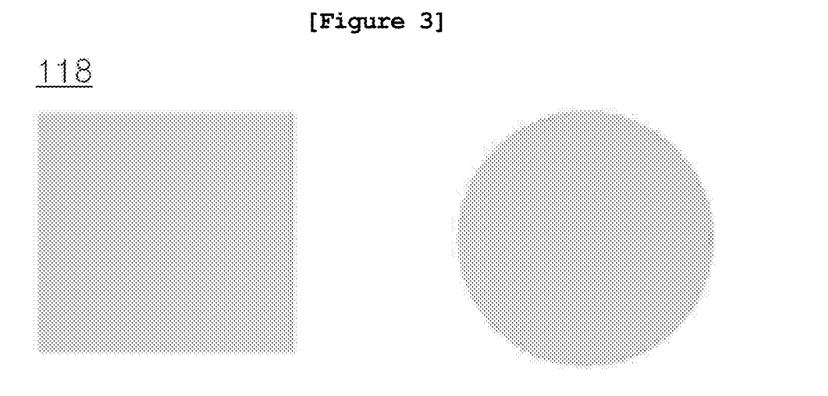
FIG. 3 is a conceptual diagram showing the shapes of a Kα X-ray filter mounted on the X-ray guides of FIG. 2.
Figure 4:
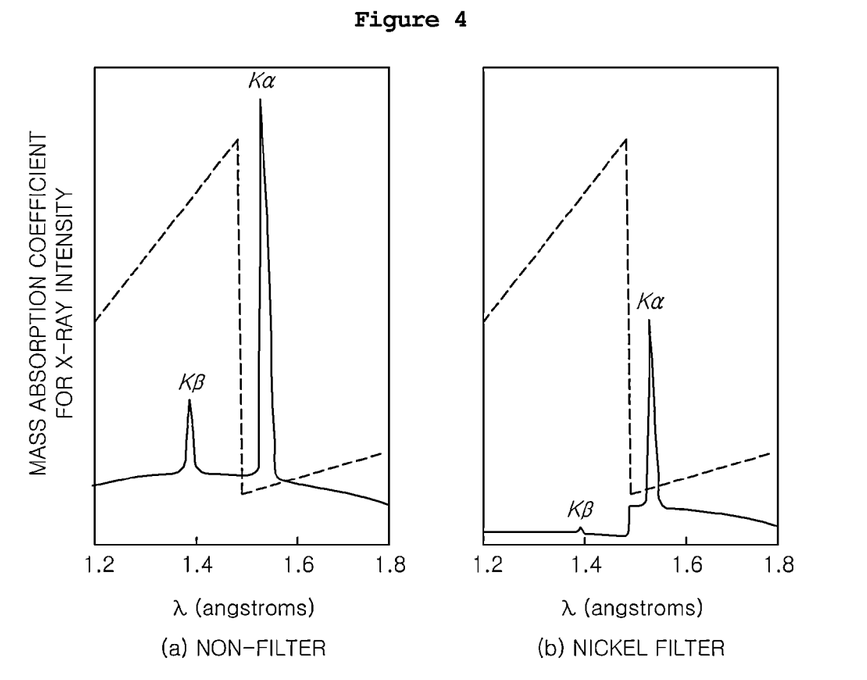
FIG. 4 is a graph showing the function of the Kα X-ray filter.

FIGS. 1a and 1b are configuration diagrams showing a non-rotational CT system according to an embodiment of the present invention, FIG. 2 is a conceptual diagram showing X-ray guides having various shapes applied to a non-rotational CT system according to an embodiment of the present invention, FIG. 3 is a conceptual diagram showing the shapes of a Kα X-ray filter mounted on the X-ray guides of FIG. 2, and FIG. 4 is a graph showing the function of the Kα X-ray filter.

Referring to FIGS. 1a and 1b, the non-rotational CT system according to the present invention includes X-ray generation units 110, X-ray detection units 120, position correction sensors 112 and 122, a control unit 130, a data processing unit 140, and an image processing unit 150. In the present invention, the X-ray generation units 110 and the X-ray detection units 120 may be respectively implemented using a plurality of X-ray generation units and a plurality of X-ray detection units. In order to describe this structure, a state in which three X-ray generation units 110 and three X-ray detection units 120 are arranged is shown in FIG. 1a. A state in which five X-ray generation units 110 and five X-ray detection units 120 are arranged is shown in FIG. 1b.

The X-ray generation units 110 are configured to generate X-rays and pass the X-rays through an examination target 200, and the X-ray detection units 120 are configured to detect X-rays having passed through the examination target 200. The plurality of X-ray generation units and the plurality of X-ray detection units may be respectively radially installed around the examination target 200. The X-ray generation units 110 and the X-ray detection units 120 may be arranged to be spaced apart from the examination target 200 by the regular distance, and the plurality of X-ray generation units 110 and X-ray detection units 120 may be simultaneously operated to perform CT scanning on the examination target 200.

In the present X-ray CT system, the X-ray generation units 110 are spaced apart from the examination target 200 by a regular distance and are radially arranged around the examination target, and are provided with position correction sensors 112 arranged in portions thereof. The X-ray detection units 120 are arranged in separated spaces between the respective X-ray generation units 110, are installed to alternate with the X-ray generation units 110, and are provided with position correction sensors 122 arranged in portions thereof. The position correction sensors 112 and 122 function to transmit data about the positions and directions of the X-ray generation units 110 and the X-ray detection units 120 to the control unit 130 according to the size of the examination target 200 requiring X-ray CT scanning.

The control unit 130 receives signals from the position correction sensors 112 and 122 arranged on the X-ray generation units 110 and the X-ray detection units 120, and adjusts the positions of corresponding X-ray generation units 110 and X-ray detection units 120 so that the corresponding X-ray generation units 110 and X-ray detection units 120 exactly face each other.

In greater detail, in the non-rotational CT system according to the present invention, the control unit 130 functions to receive signals from the position correction sensors 112 and 122 and adjust the positions and directions of the X-ray generation units 110 and the X-ray detection units 120 so that X-rays generated by one X-ray generation unit 110 can pass through the examination target 200 and can then be transferred only to an X-ray direction unit 120 designated to face the corresponding X-ray generation unit 110. Since the positions and directions can be adjusted, an unnecessary configuration may be eliminated, and thus the number of X-ray generation units 110 and the number of X-ray detection units 120 may be freely adjusted to 3, 5, or the like.

The data processing unit 140 functions to store 2D X-ray images acquired by the X-ray detection units 120 and calculate 2D X-ray images between two directions using an image interpolation technique, and the image processing unit 150 functions to convert the data of the data processing unit 140 into CT image data.

Here, an X-ray guide 115 is provided on one side of each X-ray generation unit 110 towards the examination target 200 and is preferably made of an X-ray absorbing material. FIG. 2 is a diagram showing X-ray guides having various shapes, wherein the X-ray guides may have a hollow-cylindrical shape or a rectangular parallelepiped shape. That is, the external shape of the X-ray guide is not limited to a specific shape as long as it secures a flow path for X-rays and has a hollow shape. By the structure of the X-ray guide 115, X-rays may be prevented from being scattered and interfered with and parallel X-rays with short wavelength may be generated.

In particular, when a plurality of X-ray generation units 110 are used, there is a limitation in acquiring accurate X-ray CT images due to the effect of mutual interference caused by X-rays radially generated from the respective sources. Therefore, by using the structure of the X-ray guide 115 made of the X-ray absorbing material, X-rays generated by one X-ray generation unit 110 may pass through the examination target 200 and may be transferred only to the designated X-ray detection unit 120.

A Kα X-ray filter 118 functioning to prevent mutual interference between X-rays having Kα and Kβ characteristics may be provided at the end of the X-ray guide 115 of each X-ray generation unit 110. The X-rays consist of continuous X-rays and characteristic X-rays, and the resolution of X-ray images may be deteriorated due to mutual interference between the characteristic X-rays, and thus the Kα X-ray filter 118 functions to pass only the Kα X-rays.

Further, an X-ray guide 125 is provided on one side of each X-ray detection unit 120 towards the examination target 200, is configured to enable X-rays generated by the X-ray generation unit 110 exactly facing the X-ray detection unit 120 to pass through the examination target 200 and be then transferred only to a designated X-ray detection unit 120, and is preferably made of an X-ray absorbing material. An elastic scattering prevention filter 128 may be provided at the end of the X-ray guide 125 of the X-ray detection unit 120. On the X-rays passing through the examination target 200, elastic scattering may occur, which may deteriorate the resolution of images. Accordingly, in order to prevent such elastic scattering, it is preferable to additionally install the elastic scattering prevention filter 128 on the front side of the X-ray detection unit 120. The elastic scattering prevention filter 128 may be implemented as either a mesh-type membrane made of a metal material, or a porous membrane made of a metal material.

Referring to FIGS. 3 and 4, the Kα X-ray filter has a shape identical to the hollow shape of the X-ray guide 115 provided on the X-ray generation unit 110, and the shape thereof may be changed according to the shape of the X-ray guide without being limited to a specific shape. Further, the Kα X-ray filter 118 used in the present invention may be changed according to the material of an examination target (target) in such a way that, when the target is Mo(molybdenum), the Kα X-ray filter 118 may be made of Zr(zirconium), when the target is Cu(copper), the Kα X-ray filter 118 may be made of Ni(Nickel), when the target is Co(cobalt), the Kα X-ray filter 118 may be made of Fe(iron), when the target is Fe(iron), the Kα X-ray filter 118 may be made of Mn(manganese), and when the target is Cr(Chromium), the Kα X-ray filter 118 may be made of V(vanadium) (see Table 1).

TABLE 1

Filter thickness for $\frac{I(K\alpha)}{I(K\beta)} = \frac{500}{1}$ in passed beam

| Target | Filter | Incident beam* $\frac{I(K\alpha)}{I(K\beta)}$ | mg/cm² | in | $\frac{I(K\alpha) \text{ passed}}{I(K\beta) \text{ passed}}$ |
|---|---|---|---|---|---|
| Mo | Zr | 5.4 | 77 | 0.0046 | 0.29 |
| Cu | Ni | 7.5 | 18 | 0.0008 | 0.42 |
| Co | Fe | 9.4 | 14 | 0.0007 | 0.46 |
| Fe | Mn | 9.0 | 12 | 0.0007 | 0.48 |
| Cr | V  | 8.5 | 10 | 0.0006 | 0.49 |

The transmittance of the Kα X-ray filter 118 used in each target is shown in Table 1, and the value of "I(Kα) passed/I(Kβ)incident" denotes the transmission intensity of Kα X-rays. FIG. 4 shows that when the target is made of Cu (copper) and the Kα X-ray filter 118 is made of Ni (Nickel), Kβ X-rays have scarcely passed in the case where the Kα X-ray filter 118 was used, compared to the case where the Kα X-ray filter 118 was not used, and thus it can be seen that the deterioration of the resolution of X-ray images caused by mutual interference between Kβ X-rays may be prevented.

A new image interpolation technique capable of acquiring 2D X-ray images having a minimum number of directions, calculating 2D X-ray images in various directions via image interpolation, and finally acquiring precise CT images using the 2D X-ray images by utilizing the above-described non-rotational CT system is proposed. By way of this image interpolation technique, various X-ray images of the examination target 200 are acquired every moment based on an arbitrary time point, and thereafter CT images of the examination target 200 at respective time points may be configured using a minimum number of acquired 2D X-ray images and the image interpolation technique.

For this operation, the data processing unit 140 for storing the 2D X-ray images acquired by each X-ray detection unit 120 and calculating 2D X-ray images between two directions using the image interpolation technique, and the image processing unit 150 for converting the data of the data processing unit 140 into CT image data are additionally provided. The data processing unit 140 may not only store the 2D X-ray images, but also calculate 2D X-ray images between the X-ray generation units 110. In this case, as image calculation methods, the following image interpolation technique is used.

FIG. 5a is a diagram showing an Al specimen manufactured to verify the application of an image interpolation technique, and FIG. 5b is a diagram showing comparative data between an interpolated image in a direction rotated at an angle of 7°, calculated using 2D X-ray images in directions rotated at an angle of 1° and at an angle of 13°, and a real image. That is, the drawings show images indicating results obtained by applying the image interpolation technique to 2D X-ray images acquired by a typical X-ray system and by calculating a 2D X-ray image in a direction between the two directions, and it can be seen that an image acquired through image interpolation is desirably identical to a real image.

In order to apply such an image interpolation technique, the following motion vectors based on the rotation of acquired 2D X-ray images having a minimum number of directions must be calculated.

$$\vec{v} = v_x \vec{i} + v_y \vec{j} = \frac{dx}{dt}\vec{i} + \frac{dy}{dt}\vec{j}$$

In this case, x and y denote the coordinates of a pixel at arbitrary time t, and $V_x$ and $V_y$ denote motion vectors in x and y directions, respectively. Such motion vectors may be calculated on the assumption that the value of the intensity $I(x(t), y(t), t)$ of the 2D X-ray image at an arbitrary point on the target is not changed over time or according to the rotational direction.

$$\frac{dI(x(t), y(t), t)}{dt} = 0$$

In this case, x and y denote the pixel coordinates of each image, t denotes a time at which the image is acquired, and I denotes the intensities at x and y positions at the acquisition time. If a Taylor series is applied to a differential in the above equation, intensity I at arbitrary time t+dt may be represented by the following equation:

$$I(x+dx, y+dy, t+dt) = I(x, y, t) + \frac{\partial I}{\partial x}dx + \frac{\partial I}{\partial y}dy + \frac{\partial I}{\partial t}dt$$

When this equation is applied to an equation based on the assumption that the intensity of an image is preserved, the following equation may be obtained.

$$\frac{dI}{dt} + \frac{\partial I}{\partial x}\frac{dx}{dt} + \frac{\partial I}{\partial y}\frac{dy}{dt} + \frac{\partial I}{\partial t}\frac{dt}{dt} = 0$$

Since a first term in the equation becomes "0" according to the image preservation assumption, the equation may be represented by the following equation:

$$\frac{\partial I}{\partial x}v_x + \frac{\partial I}{\partial y}v_y + \frac{\partial I}{\partial t} = 0$$

This equation may be simply represented by the following equation:

$$I_x \cdot v_x + I_y \cdot v_y = -I_t$$

where $$I_x = \frac{\partial I}{\partial x}, I_y = \frac{\partial I}{\partial y}, \text{ and } I_t = \frac{\partial I}{\partial t}$$

denote differential values of the image intensity for x, y, and t, respectively. In order to directly calculate motion vectors, a Lucas-Kanade algorithm may be used. When individual pixels of one image are taken into consideration, the above equation may be represented by the following determinant:

$$\begin{cases} I_x(q_1) \cdot V_x + I_y(q_1) \cdot V_x = -I_t(q_1) \\ I_x(q_2) \cdot V_x + I_y(q_2) \cdot V_x = -I_t(q_2) \\ \vdots \quad \vdots \quad \vdots \\ I_x(q_n) \cdot V_x + I_y(q_n) \cdot V_x = -I_t(q_n) \end{cases}$$

where $q_i$ denotes each pixel, and the motion vector may be calculated by the following determinant:

$$\begin{bmatrix} V_x \\ V_y \end{bmatrix} = \begin{bmatrix} \sum_i I_x(q_i)^2 & \sum_i I_x(q_i)I_y(q_i) \\ \sum_i I_x(q_i)I_y(q_i) & \sum_i I_y(q_i)^2 \end{bmatrix}^{-1} \begin{bmatrix} \sum_i I_x(q_i)I_t(q_i) \\ \sum_i I_y(q_i)I_t(q_i) \end{bmatrix}$$

When the motion vector is calculated, the positions $x_p$ and $y_p$ and intensity $I_p(x_p, y_p)$ of an i-th pixel to be interpolated at arbitrary time point $$t_p = t_\alpha + \frac{m}{n}\Delta t$$

may be calculated as follows by using the two real X-ray images at time points $t_\alpha$ and $t_\beta$ corresponding to X-ray radiation angles α and β, respectively. In this case, $t_p$ denotes time corresponding to an angle at which image interpolation is performed, and $\Delta t = t_\beta - t_\alpha$ denotes a normalized time, which is regarded as '1.'

$$x_p = x_i(t_\alpha) + \frac{m}{n}v_x\Delta t, \quad (m = 1, 2, \ldots, n-1)$$

-continued $$y_p = y_i(t_\alpha) + \frac{m}{n} v_y \Delta t, \quad (m = 1, 2, \ldots, n-1)$$

$$I_p(x_p, y_p) = I(x_i(t_\alpha), y_i(t_\alpha)) + \frac{m}{n}(I(x_i(t_\beta), y_i(t_\beta)) - I(x_i(t_\alpha), y_i(t_\alpha))), \quad (m = 1, 2, \ldots, n-1)$$

In this case, 'n' denotes the number of constant angle intervals at which image interpolation is to be performed, and 'm' denotes a constant indicating the number of times that image interpolation is performed. Considering $\alpha=0°$ and $\beta=90°$, interpolated images may be acquired at intervals of 30° between the two angles when n=3, and interpolated images may be acquired at intervals of 18° when n=5. Further, when m=1, an interpolated image may be acquired at an angle of 30°, and when m=2, an interpolated image may be acquired at an angle of 60°.

Figure 5:
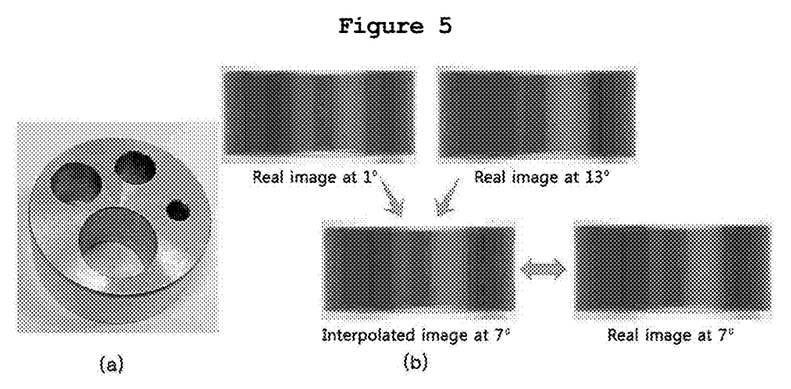
FIG. 5a is a diagram showing an Al specimen manufactured to verify the application of an image interpolation technique.
FIG. 5b is a diagram showing comparative data between an interpolated image in a direction rotated at an angle of 7°, calculated using 2D X-ray images in directions rotated at an angle of 1° and at an angle of 13°, and a real image.

2D X-ray images in directions rotated at an angle of 1° and at an angle of 13° with respect to a reference direction are acquired using a Al specimen manufactured to verify the validity of the image interpolation technique, and thereafter an interpolated image in a direction rotated at an angle of 7° is calculated using the two acquired images and is compared with a real X-ray image acquired in a direction rotated at an angle of 7°, and then resulting images are shown in FIG. 5.

It can be seen in FIG. 5 that an image, calculated via interpolation, and a real image are desirably identical to each other.

Figure 6:
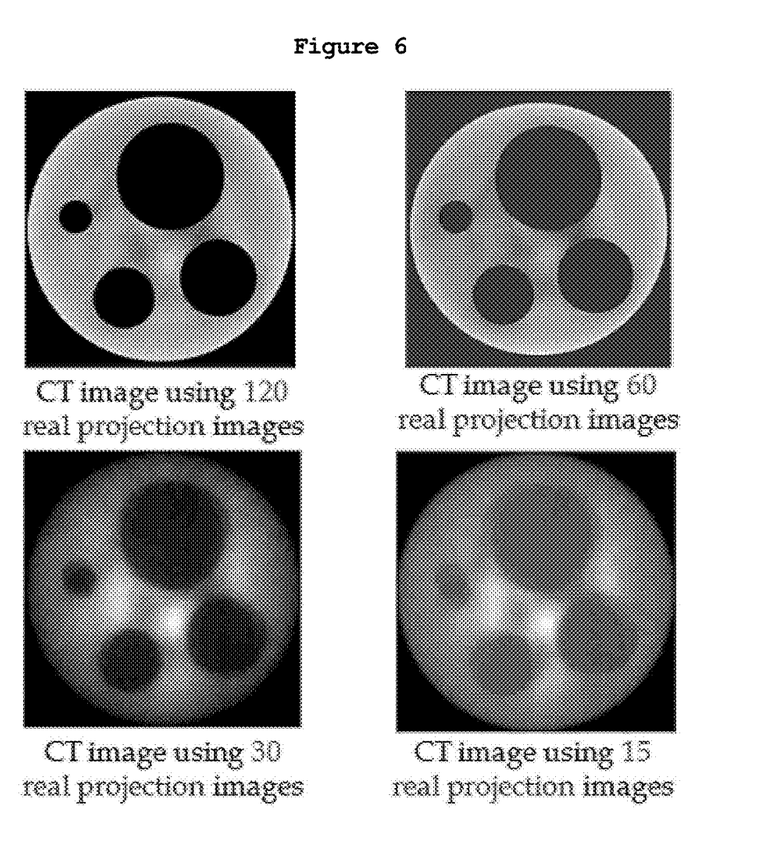
FIG. 6 is a diagram showing images acquired by an OSEM technique for acquiring CT images using an interpolated image.

FIG. 6 is a diagram showing images acquired using the following Ordered Subset Expectation Maximization (OSEM) technique, which is a technique for acquiring CT images using interpolated images, wherein it may be determined whether the quality of CT images has deteriorated depending on a decrease in the number of 2D X-ray images:

$$x_j^{n+1} = \frac{x_j^n}{\sum_{j=1}^{N} p(i/j)} \sum_{i=1}^{M} \frac{y_i p(i/j)}{x_j^n p(i/j)}, \quad j = 1, 2, \ldots, L$$

where $x_j^{n+1}$ denotes the intensity of pixel $x_j$ at (n+1) iterations, M and N denote the number of rows and the number of columns of pixels of the corresponding 2D X-ray image, L denotes the number of subsets, p(i/j) denotes an expectation function of a j-th X-ray that reaches an i-th detector pixel, and $y_i$ denotes electron emission data.

Referring to FIG. 6, it can be seen that, when 120 2D X-ray images and 60 2D X-ray images are used, high-resolution CT images may be calculated, whereas when 30 2D X-ray images and 15 2D X-ray images are used, low-resolution CT images may be calculated. This is the limitation of a typical CT image acquisition technique.

Figure 7:
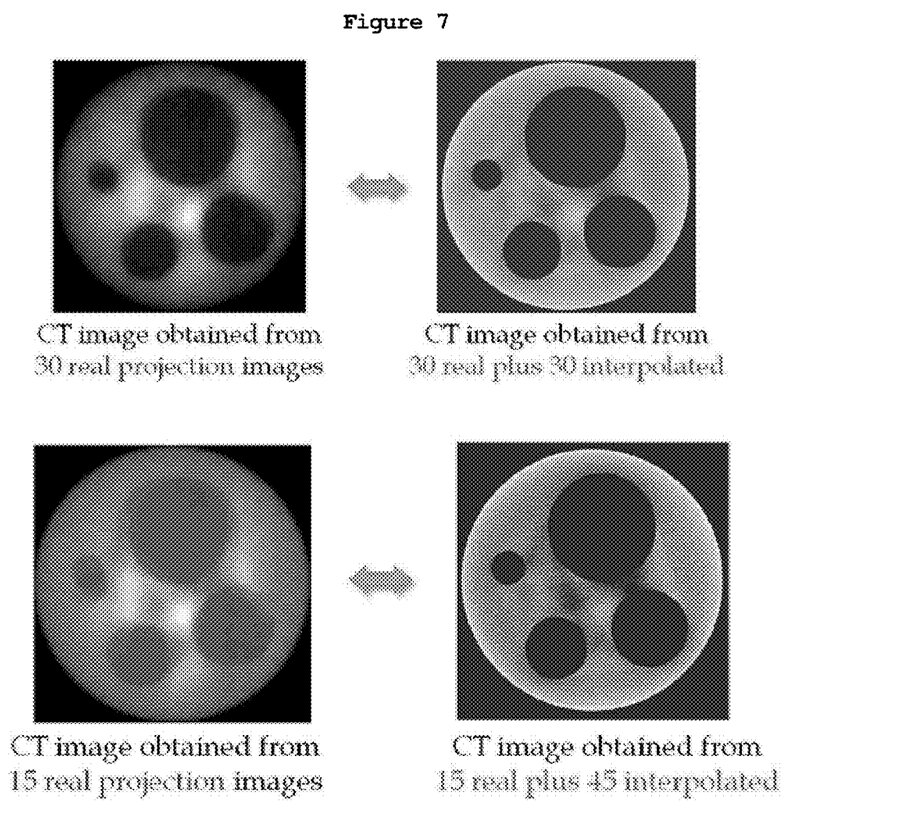
FIG. 7 is a diagram showing the results of CT images improved after an image interpolation technique has been applied to 30 and 15 real projection images.

FIG. 7 is a diagram showing the results of improved CT images after an image interpolation technique has been used, and shows that, when CT images are calculated using 30 2D X-ray interpolated images, acquired by the image interpolation technique in the present research, and 30 real 2D X-ray images, the low resolution of CT images acquired using 30 or 15 real 2D X-ray images may be greatly improved.

Figure 8:
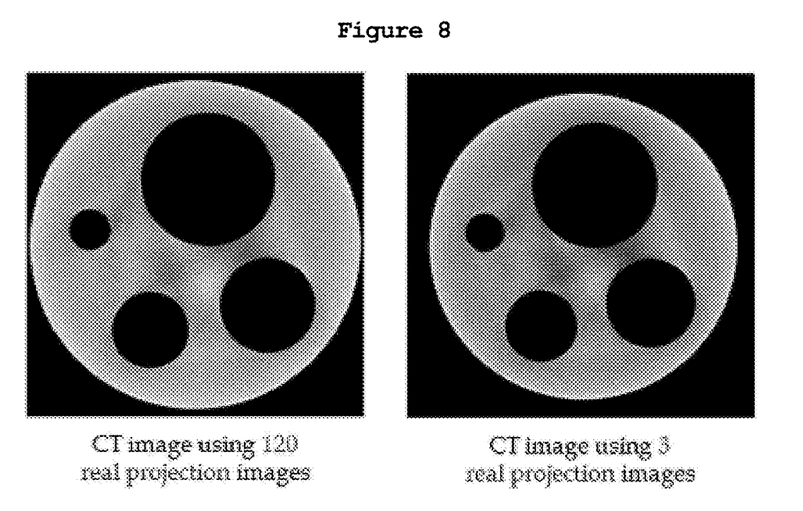
FIG. 8 is a diagram showing the results of a comparison between images, improved after an image interpolation technique has been applied to 3 real projection images, and 120 real projection images.

When such an image interpolation technique is used, high-resolution CT images may be acquired using only 3 real X-ray images, and the results thereof are shown in FIG. 8.

Figure 9:
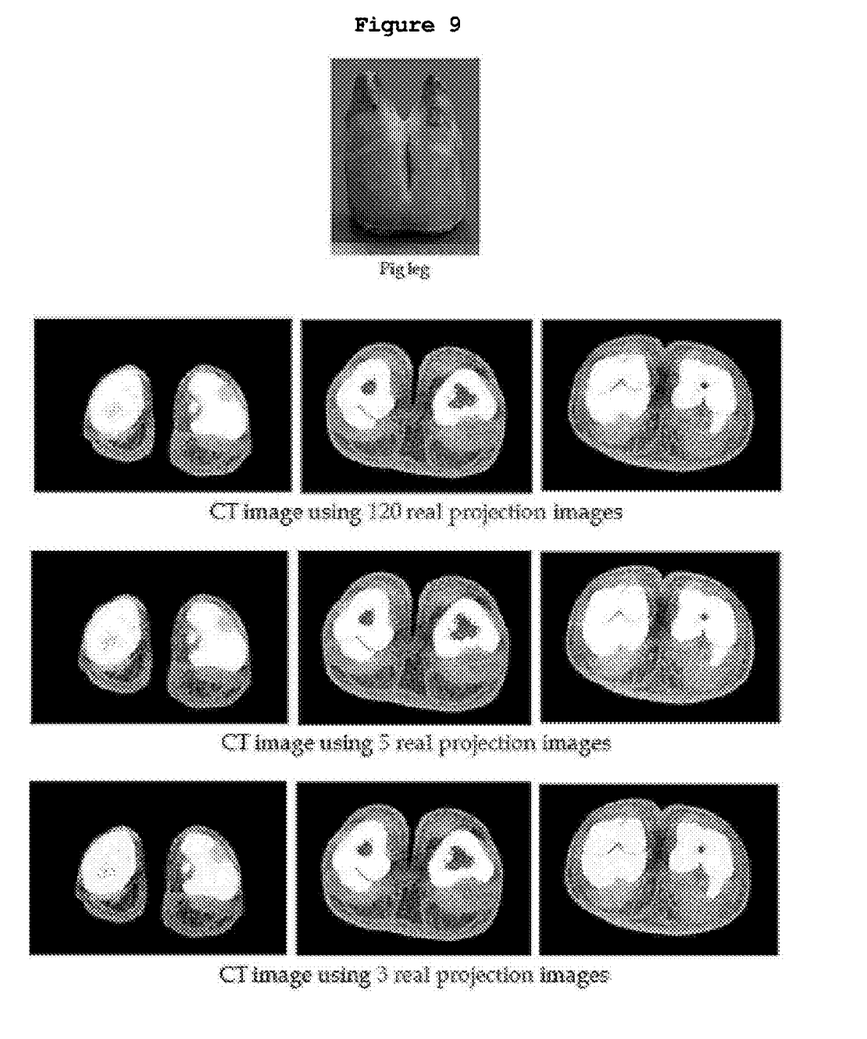
FIG. 9 is a diagram showing the results of a comparison between images when the leg of a pig has been used as a specimen so as to determine the applicability to a biological specimen having a complicated structure, such as a human body, improved CT images have been acquired by individually applying an image interpolation technique to 5 real projection images and 3 real projection images, and the improved CT images are compared with images acquired by applying an Ordered Subset Expectation Maximization (OSEM) technique to 120 real projection images.

In order to apply the present technique to complicated biological specimens, such as a human body, and verify the technique, experiments were conducted using the tip of the foot of a pig. It can be seen in FIG. 9 that, in the case of biological specimens having a complicated structure, CT images having precision similar to that of CT images acquired after an OSEM technique has been applied to 120 X-ray images may be acquired when the image interpolation technique is applied to 3 or 5 real X-ray images.

As described above, the finally acquired CT images are externally displayed as video data on a separate display device.

When the non-rotational CT system according to the present invention is used, radiation exposure to patients may be remarkably reduced, CT images of regions of patients having motions, that is, the backbone, joints, the heart, etc., at arbitrary time points may be acquired, and more substantial image diagnostic data of patients may be secured by means of such CT images. Further, variations in the internal structures of various objects having a deformation or movement, with respect to the states of the objects at respective time points, may be examined.

Further, in the present invention, X-ray guides may be adopted, so that the deterioration of image sensitivity caused by interference between X-rays generated by a plurality of X-ray generation units may be prevented, and the deterioration of data sensitivity caused by phase shift and interference of X-rays may be prevented.

Although the preferred embodiments of the present invention have been disclosed, the present invention is not limited to the above-described specific embodiments. That is, those skilled in the art to which the present invention pertains may implement a plurality of changes and modifications of the present invention without departing from the scope and spirit of the invention as disclosed in the accompanying claims, and equivalents of all suitable changes and modifications should be interpreted as being included in the scope of the present invention.

The invention claimed is:

1. A non-rotational Computerized Tomography (CT) system, comprising:
   a plurality of X-ray generation units spaced apart from an examination target by a regular distance and radially arranged around the examination target, the X-ray generation units having position correction sensors arranged in portions thereof;
   a plurality of X-ray detection units arranged in separated spaces between the X-ray generation units and installed to alternate with the X-ray generation units, the X-ray detection units having position correction sensors arranged in portions thereof; and
   a control unit configured to receive signals from the position correction sensors arranged on the X-ray generation units and the X-ray detection units, and adjust positions of corresponding X-ray generation units and X-ray detection units so that the corresponding X-ray generation units and X-ray detection units exactly face each other,
   wherein
   each of the X-ray detection units includes an X-ray guide provided on a first side thereof towards the examination target, and is configured to allow X-rays generated by an X-ray generation unit exactly facing the corresponding X-ray detection unit to pass through the examination target and to be then transferred only to a designated X-ray detection unit; and
   each of the X-ray detection units includes an elastic scattering prevention filter arranged at an end of the X-ray guide of the X-ray detection unit.

2. The non-rotational CT system of claim 1, wherein each of the X-ray generation units includes an X-ray guide provided on a first side thereof towards the examination target.

3. The non-rotational CT system of claim 2, wherein the X-ray guides of the X-ray generation units and the X-ray detection units are made of an X-ray absorbing material.

4. The non-rotational CT system of claim 2, wherein each of the X-ray generation units includes a Kα X-ray filter disposed at an end of the X-ray guide of the X-ray generation unit and configured to function to prevent mutual interference between X-rays having Kα and Kβ characteristics.

5. The non-rotational CT system of claim 1, wherein the control unit receives signals from the position correction sensors, and adjusts positions and directions of the X-ray generation units and the X-ray detection units so that X-rays generated by one X-ray generation unit pass through the examination target and can then be transferred only to an X-ray detection unit designated to face the corresponding X-ray generation unit.

6. A non-rotational Computerized Tomography (CT) system, comprising:
  a plurality of X-ray generation units spaced apart from an examination target by a regular distance and radially arranged around the examination target, the X-ray generation units having position correction sensors arranged in portions thereof;
  a plurality of X-ray detection units arranged in separated spaces between the X-ray generation units and installed to alternate with the X-ray generation units, the X-ray detection units having position correction sensors arranged in portions thereof;
  a control unit configured to receive signals from the position correction sensors arranged on the X-ray generation units and the X-ray detection units, and adjust positions of corresponding X-ray generation units and X-ray detection units so that the corresponding X-ray generation units and X-ray detection units exactly face each other;
  a data processing unit configured to store 2D X-ray images acquired by the X-ray detection units and calculate 2D X-ray images between two directions using an image interpolation technique; and
  an image processing unit configured to convert data of the data processing unit into CT image data,
  wherein
  each of the X-ray detection units includes an X-ray guide provided on a first side thereof towards the examination target, and is configured to allow X-rays generated by an X-ray generation unit exactly facing the corresponding X-ray detection unit to pass through the examination target and to be then transferred only to a designated X-ray detection unit; and
  each of the X-ray detection units includes an elastic scattering prevention filter arranged at an end of the X-ray guide of the X-ray detection unit.

7. The non-rotational CT system of claim 6, wherein each of the X-ray generation units includes an X-ray guide provided on a first side thereof towards the examination target.

8. The non-rotational CT system of claim 7, wherein the X-ray guides of the X-ray generation units and the X-ray detection units are made of an X-ray absorbing material.

9. The non-rotational CT system of claim 7, wherein each of the X-ray generation units includes a Kα X-ray filter disposed at an end of the X-ray guide of the X-ray generation unit and configured to function to prevent mutual interference between X-rays having Kα and Kβ characteristics.

10. The non-rotational CT system of claim 6, wherein the control unit receives signals from the position correction sensors, and adjusts positions and directions of the X-ray generation units and the X-ray detection units so that X-rays generated by one X-ray generation unit pass through the examination target and is then transferred only to an X-ray detection unit designated to face the corresponding X-ray generation unit.

11. The non-rotational CT system of claim 6, wherein the 2D X-ray data acquired using the image interpolation technique is obtained by converting images into CT image data using an Ordered Subset Expectation Maximization (OSEM) technique.

* * * * *